United States Patent [19]
Hoffman et al.

[11] Patent Number: 6,137,857
[45] Date of Patent: Oct. 24, 2000

[54] SCALABLE DETECTOR FOR COMPUTED TOMOGRAPH SYSTEM

[75] Inventors: David M. Hoffman, New Berlin; August O. Englert, Waukesha, both of Wis.

[73] Assignee: General Electric Company, Milwaukee, Wis.

[21] Appl. No.: 08/979,011

[22] Filed: Nov. 26, 1997

[51] Int. Cl.[7] .................................................. G01N 23/00
[52] U.S. Cl. ................................................. 378/19; 378/4
[58] Field of Search .......................................... 378/19, 4

[56] References Cited

U.S. PATENT DOCUMENTS

| | | | |
|---|---|---|---|
| 4,338,521 | 7/1982 | Shaw et al. | 250/370.11 |
| 4,965,726 | 10/1990 | Heuscher et al. | 378/19 |
| 5,592,523 | 1/1997 | Tuy et al. | 378/19 |

FOREIGN PATENT DOCUMENTS 6-169912  6/1994  Japan ....................................... 378/19

*Primary Examiner*—Craig E. Church
*Attorney, Agent, or Firm*—Armstrong Teasdale; Christian G. Cabou; Phyllis Y. Price

[57] ABSTRACT

A multislice detector array producing an alterable quantity of slices and slice resolutions. In one embodiment, the detector array includes a detector housing, a plurality of detector modules, and a collimator. Each detector module includes a plurality of photodiodes arranged in an array of rows and columns, a switch apparatus electrically coupled to the photodiode output signals, and a decoder. The collimator is configured to separate X-ray beams so that only the focal X-ray beams are impinged upon the detector modules.

20 Claims, 4 Drawing Sheets

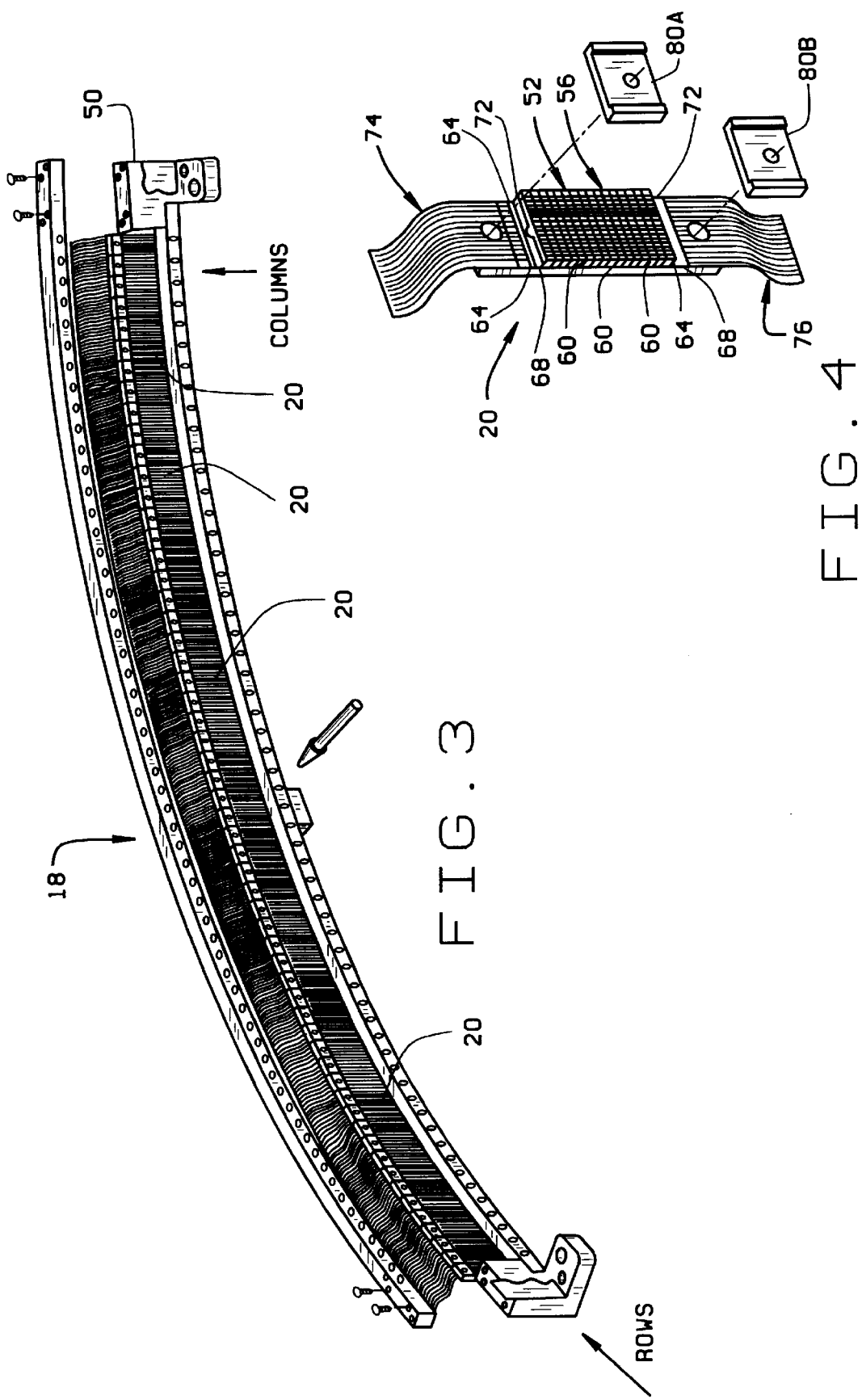

SCALABLE DETECTOR FOR COMPUTED TOMOGRAPH SYSTEM

FIELD OF THE INVENTION

This invention relates generally to computed tomograph (CT) imaging and, more particularly, to detectors utilized in connection with CT systems.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector. A scintillator is located adjacent the collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

Multislice detectors may have multiple detector elements in the X and Z directions to increase spatial resolution. These elements can be separated by narrow gaps of only a few mils between adjacent elements. The gaps are filled with a light reflecting material. The detector elements could accept off-axis, or scattered, x-ray beams which decrease contrast resolution.

Accordingly, it would be desirable to provide a detector array that collimates and separates the x-ray beams toward individual detector elements. In addition, it is desirable to provide a detector array collimator that protects the gaps between the elements from x-rays so that radiation damage of the reflecting material is minimized. It is also desirable to provide a detector array collimator that reduces penetration of the x-rays towards the photodiodes.

SUMMARY OF THE INVENTION

These and other objects may be attained by a detector array, which in one embodiment, enables modification of the quantity of slices and slice resolution, or slice thickness. The detector array includes a detector housing, a plurality of detector modules and a collimator. Each detector module is mounted to the detector housing and includes a photodiode array optically coupled to a scintillator array. The photodiode array includes a plurality of photodiodes arranged in rows and columns. The collimator is aligned and positioned adjacent to the scintillator array and separates the X-ray beams so that the X-ray beams that pass through the collimator correspond to the scintillator array.

Each detector module further includes a switch apparatus and a decoder. The switch apparatus is electrically coupled between the photodiode output lines and a CT system data acquisition system (DAS). The switch apparatus, in one embodiment, is an array of field effect transistors (FETs) and alters the number of slices and the thickness of each slice by allowing each photodiode output line to be enabled, disabled, or combined with other photodiode output lines.

In one embodiment, each detector module is fabricated by depositing, or forming, the photodiode array, the switch apparatus, and the decoder on a substrate. Each photodiode output line is electrically connected to the switch apparatus. The switch apparatus output and decoder control lines are then electrically coupled to the first end of a flex cable. After installing the detector modules into the detector array, the second end of the flex cable is electrically connected to the DAS.

The collimator is fabricated by spacing and securing together a plurality of plates so that the longitudinal axis of each plate extends parallel to the longitudinal axis of the other plates, and each plate is focally aligned. In one embodiment, one wire is then extended the length of the collimator perpendicular to the longitudinal axis plates forming a plurality of sections. The number of sections corresponds to the size of the photodiode array so that the X-ray beams are separated to correspond to the number of photodiode array rows and columns.

The above described detector array enables selection of the number of slices of data to be electrically transmitted for each rotation of the CT system. In addition, the detector collimator allows the X-ray beams to be separated so that only the focal X-ray beams are transmitted to the scintillator array resulting in more accurate scan data. Additionally, the detector modules allows the slice thickness to be selected to produce various slice resolutions. As a result, the configuration of the detector module can be altered to accommodate the specific needs and requirements of a test.

BRIEF DESCRIPTION OF THE DRAWINGS

FIG. 3 is a perspective view of a CT system detector array in accordance with the present invention.

FIG. 4 is a perspective view of a detector module shown in FIG. 3.

DETAILED DESCRIPTION

Figure 1:
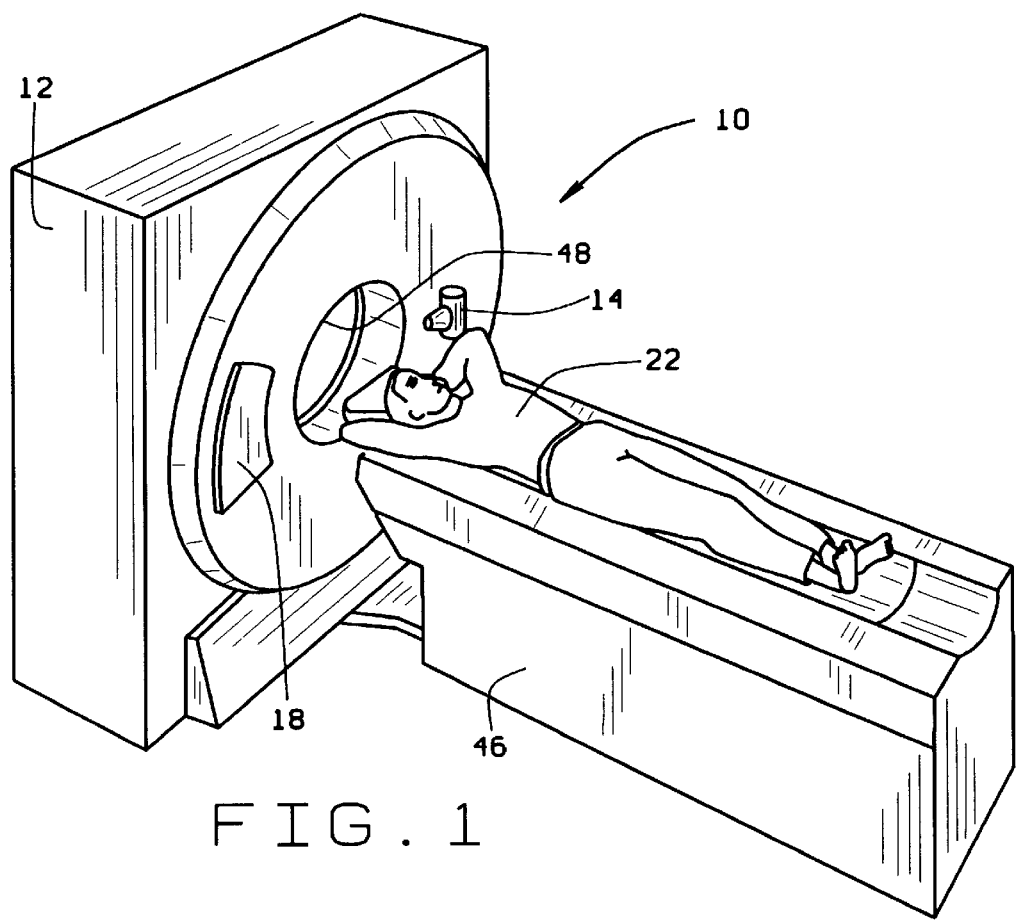
FIG. 1 is a pictorial view of a CT imaging system.
Figure 2:
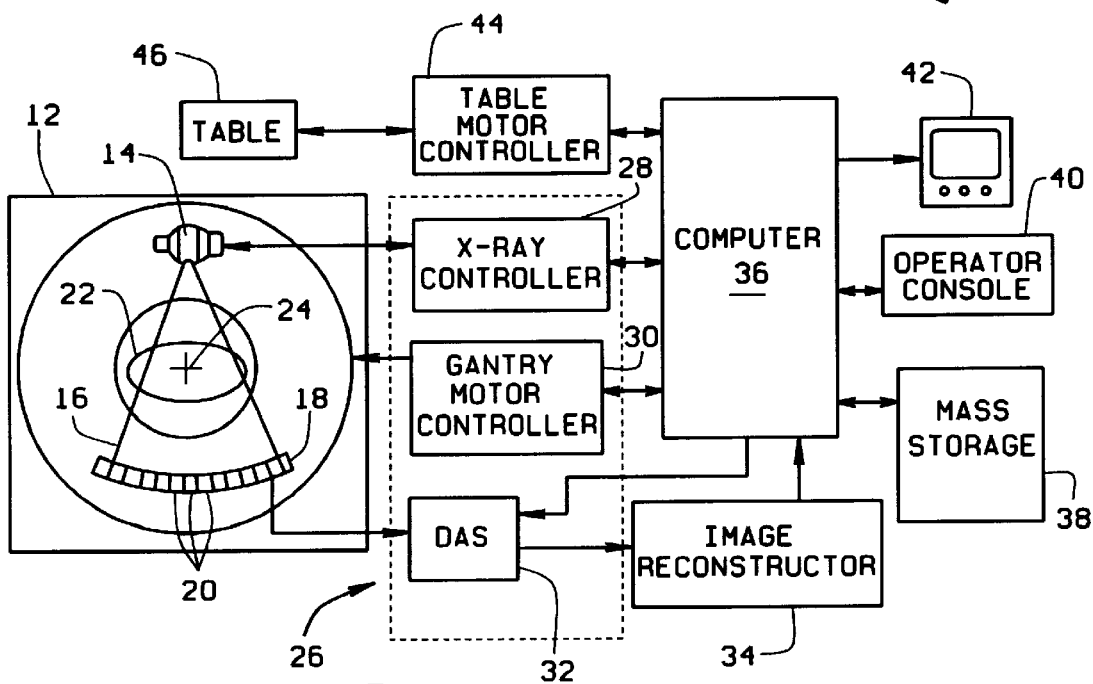
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces electrical signals that represent the intensity of impinging x-ray beams and hence the attenuation of the beams as they pass through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48.

As shown in FIGS. 3 and 4, detector array 18 includes a plurality of detector modules 20 secured to an arch shaped detector housing 50. Each detector module 20 includes a multidimensional photodiode array 52 and a multidimensional scintillator array 56 positioned in front of and adjacent to photodiode array 52. One photodiode array that may be used is described in copending U.S. patent application Ser. No. (15-CT-4631), entitled, Photodiode Array For A Scalable Multislice Scanning Computed Tomography System, which is assigned to the present assignee and hereby incorporated herein, in its entirety, by reference. One scintillator array that may be used is described in copending U.S. patent application Ser. No. (15-CT-4513), entitled, Scintillator For A Multi-slice Computed Tomograph System, which is assigned to the present assignee and hereby incorporated herein, in its entirety, by reference. Detector array 18 also includes a collimator 54 positioned in front of and adjacent scintillator array 56 to collimate x-ray beams 16 before such beams impinge upon scintillator array 56. Photodiode array 52 includes a plurality of photodiodes 60 which are optically coupled to scintillator array 56. Photodiodes 60 generate electrical output signals 62 representative of the light output by each scintillator of scintillator array 56.

Figure 5:
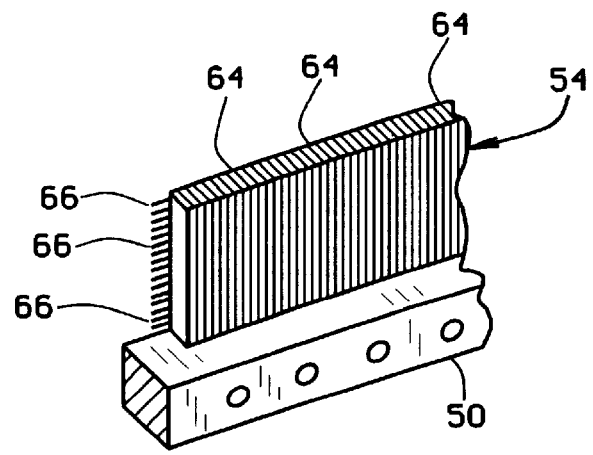
FIG. 5 is a perspective view of a collimator in accordance with the present invention.

Referring to FIG. 5, collimator 54 includes a plurality of plates 64 and at least one wire 66. Plates 64 are spaced and secured together so that the longitudinal axis of each plate 64 extends substantially parallel to the longitudinal axis of each adjacent plate 64. Plates 64 are inserted in slots (not shown) located in housing 50 and bonded at the top and bottom of plates 64. Plates 64 and wire 66 are made, in one embodiment, of tungsten. Wire 66 extends the length of collimator 54 substantially perpendicular to the longitudinal axis of plates 66 and is inserted in horizontal slots (not shown) in plates 64 and bonded.

Plates 64 and wire 66 create a plurality of sections (not shown) with each section having an active area and an inactive area (not shown). The active areas are approximately equal in size and separate X-rays 16 so that only the focal x-ray beams are allowed to pass through collimator 54 to scintillator array 56. Inactive areas prevent non-focal x-rays beams from impinging upon scintillator array 56 and photodiode 52. The number of sections is dependent on the size of scintillator array 56 and photodiode array 52. The area of scintillator array 56 directly below wire 66 is protected from impinging x-ray beams 16. For example, wire 66 may be positioned above each scintillator array gap (not shown) to protect reflective material from radiation damage and reduce penetration of x-ray beams 16 toward photodiode array 52. In one embodiment, the number of collimator wires 66 is one greater than the number of rows in scintillator array 56 so that each gap is protected.

For example, in a sixteen slice mode of operation, detector array 18 includes fifty-seven detector modules 20. Each detector module 20 includes a photodiode array 52 and scintillator array 56, each having an array size of 16 ×16 so that array 18 has 16 rows and 912 columns (16×57 modules). As a result, collimator 54 includes seventeen wires 66 and 913 plates 64 allowing 16 simultaneous slices of data to be collected with each rotation of gantry 12. Additional examples include, a two slice mode of operation including three wire 66; and a four slice mode of operation including five wires 66. Additional modes beyond those described are possible.

Detector module 20 also includes a switch apparatus 68 electrically coupled to a decoder 72. Switch apparatus 68 is a multidimensional semiconductor switch array of similar size as photodiode array 52. In one embodiment, switch apparatus 68 includes an array of field effect transistors (not shown) with each field effect transistor (FET) having an input, an output, and a control line (not shown). Switch apparatus 68 is coupled between photodiode array 52 and DAS 32. Particularly, each switch apparatus FET input is electrically connected to a photodiode array output 62 and each switch apparatus FET output is electrically connected to DAS 32, for example, using flexible electrical cables 74 and 76. Cables 74 and 76 are secured to detector module 20 with respective mounting blocks 80A and 80B.

Decoder 72 controls the operation of switch apparatus 68 to enable, disable, or combine photodiode outputs 62 in accordance with a desired number of slices and slice resolutions for each slice. Decoder 72, in one embodiment, is a decoder chip or a FET controller as known in the art. Decoder 72 includes a plurality of output and control lines coupled to switch apparatus and computer 36. Particularly, the decoder outputs are electrically connected to the switch apparatus control lines to enable switch a apparatus 68 to transmit the proper data from the switch apparatus inputs to the switch apparatus outputs. The decoder control lines are electrically connected to the switch apparatus control lines and determine which of the decoder outputs will be enabled. Utilizing decoder 72, specific FETs within switch apparatus 68 are enabled, disable, or combined so that specific photodiode outputs 62 are electrically connected to CT system DAS 32. In one embodiment defined as a 16 slice mode, decoder 72 enables switch apparatus 68 so that all rows of photodiode array 52 are electrically connected to DAS 32, resulting in 16 separate, simultaneous slices of data being sent to DAS 32. Of course, many other slice combinations are possible.

Figure 6:
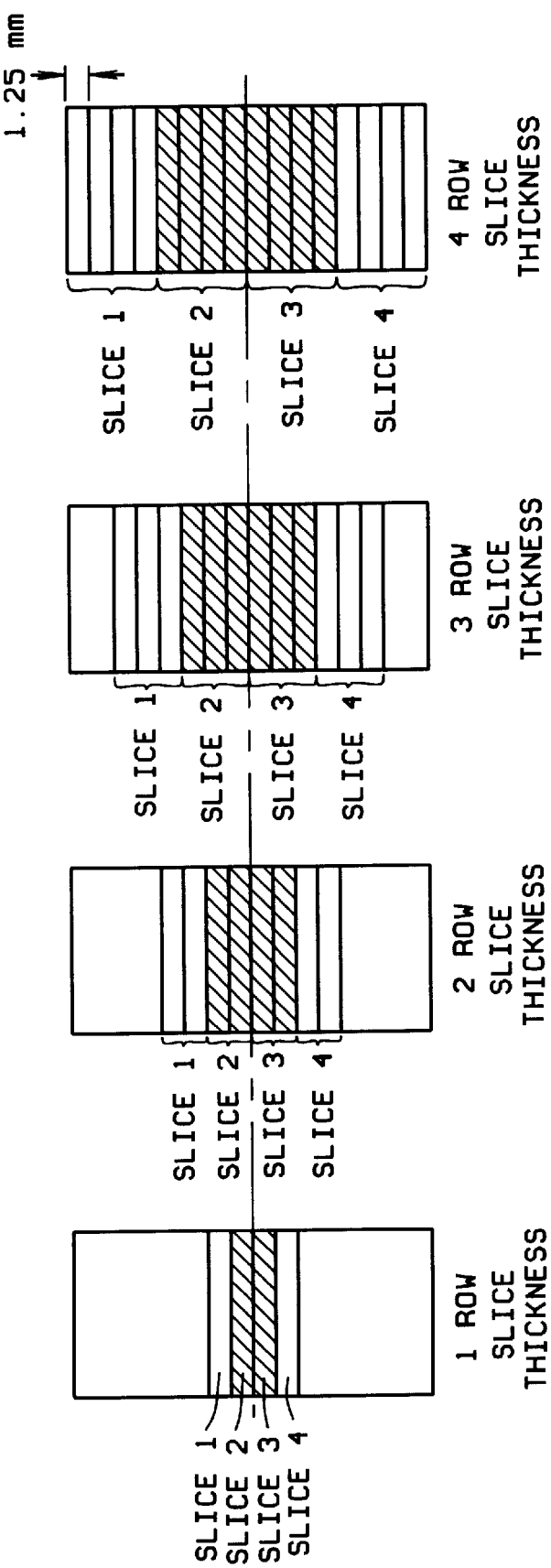
FIG. 6 is a front view of a detector module shown in FIG. 4.

For example, decoder 72 may also select from other multiple slice modes, including one, two, and four slice modes. As shown in FIG. 6, by activating the appropriate decoder control lines, switch apparatus 68 can be configured in the four slice mode so that data is collected from four slices of one or more rows of photodiode array 52. Depending upon the specific configuration of switch apparatus 68 as defined by decoder control lines, various combinations of photodiode outputs 62 can be enabled, disabled, or combined so that the thickness of each slice may be 1, 2, 3, or 4 rows. Additional examples include, a single slice mode including one slice with slices ranging from 1 row to 16 rows thick; and a two slice mode including two slices with slices ranging from 1 row to 8 rows thick. Additional modes beyond those described are possible where the total number of photodiode array element rows, or pixels per channel, is equal to the number of slices or FET outputs times the number of rows per slice. For example, in a 4 slice mode of operation using 4 rows per slice, photodiode and scintillator arrays 52 and 56 include at least 16 rows of elements and switch apparatus 68 includes at least 4 FET outputs. In one embodiment, for example, each row is 1.25 mm wide.

Figure 7:
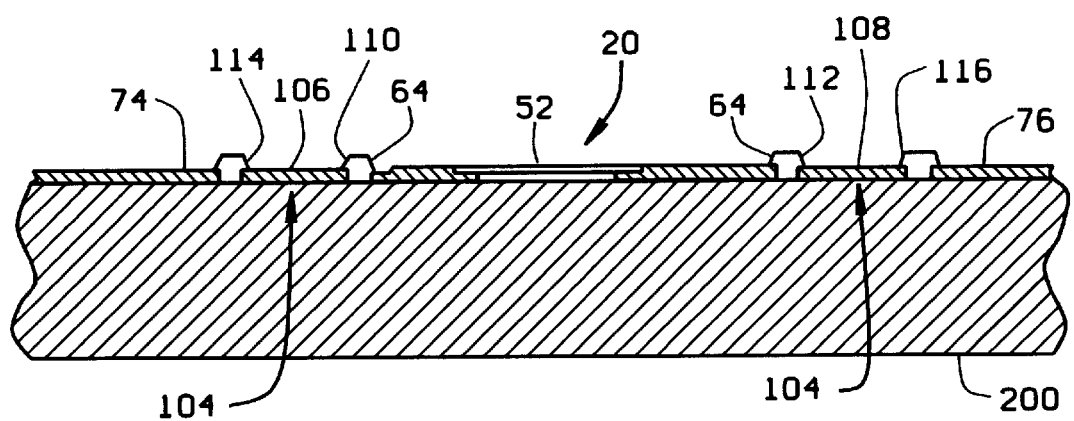
FIG. 7 is a side view of a portion of the detector module shown in FIG. 4.

In one embodiment and referring to FIG. 7, switch apparatus 68 and decoder 72 are combined into a FET array 104. FET array 104 includes a plurality of field effect transistors (FET) (not shown) arranged as a multidimensional array. In one embodiment, two semiconductor devices 106 and 108 are utilized so that one-half of photodiode output lines 62 are connected to device 106 and one-half of photodiode output lines 62 are connected to device 108. FET arrays 106 and 108 each include respective input lines 110 and 112, output lines 114 and 116, and control lines (not shown). Internal to device 106, input lines 110 are electrically connected to the switch apparatus input lines, output lines 114 are electrically connected to the switch apparatus output lines, and decoder output lines are electrically connected to FET control lines. Switch 108 is internally configured identical to switch 106.

In fabrication of detector module 20, photodiode array 52 including scintillator array 56 and FET arrays 106 and 108 are deposited, or formed, on substrate 200 so that photodiode outputs 62 are adjacent arrays 106 and 108. Photodiode outputs 62 are then connected to inputs 110 and 112 of respective FET arrays 106 and 108. Particularly, one-half of photodiode outputs 62 are wire bonded to FET array inputs 110 and one-half of photodiode outputs 62 are wire bonded to respective FET array inputs 112 so that each output 62 is electrically connected to a FET input line. Photodiode outputs are wire bonded to FET input lines using various wire bonding techniques, including, for example, aluminum wire wedge bonding and gold wire ball bonding as known in the art. First ends of flexible electrical cables 74 and 76 are then electrically connected and secured to FET arrays 106 and 108. FET array output and control lines are electrically connected to cables 74 and 76. Particularly, each FET array output line 114 and 116 is wire bonded to a wire of respective cables 74 and 76. Detector module 20 is completed by securing first ends of cables 74 and 76 with respective mounting blocks 80A and 80B.

After fabricating detector modules 20 as described above, detector modules 20 are mechanically mounted onto housing 50 so that scintillator arrays 56 are positioned adjacent to collimator 54 and form array 18. Second ends of cables 74 and 76 of each detector module 20 are then electrically connected to CT system DAS 32.

In operation, the operator determines the number of slices and thickness of each slice. The appropriate configuration information is transmitted to the array control lines to configure switch apparatus 68 using decoder 72. As X-ray beams 16 are projected toward detector array 18, collimator 54 allows only the focal X-ray beams to impinge upon detector modules 20. As a result, data for the selected configuration is transmitted to DAS 32.

The above described detector array enables selection of the number of slices of data to be electrically transmitted for each rotation of the CT system. In addition, the detector collimator allows the X-ray beams to be separated so that only the focal X-ray beams are transmitted to the scintillator array resulting in more accurate scan data. Additionally, the detector modules allows the slice thickness to be selected to produce various slice resolutions. As a result, the configuration of the detector module can be altered to accommodate the specific needs and requirements of a test.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A collimator for a multislice computed tomography machine, said collimator comprising a plurality of plates, each of said plates having a longitudinal axis extending substantially parallel to a longitudinal axis of an adjacent one of said plates; and at least one wire extending substantially perpendicular to said longitudinal axis of each said plate, said wire dividing said collimator into a plurality of sections, said collimator adapted for use in multiple slice modes of operation.

2. A collimator in accordance with claim 1 wherein for a two slice mode of operation, said collimator is divided into two sections by a wire extending substantially perpendicular to said longitudinal axis of said plates.

3. A collimator in accordance with claim 2 wherein an active area of one of said sections is approximately equal to an active area of said other section.

4. A collimator in accordance with claim 1 wherein for an n slice mode of operation, said collimator is divided into n sections by n+1 wires extending substantially perpendicular to said longitudinal axis of said plates where n equals the number of slices.

5. A collimator in accordance with claim 4 wherein an active area of each of said sections is approximately equal to an active area of said other sections.

6. A collimator in accordance with claim 1 wherein for a sixteen slice mode of operation, said collimator is divided into sixteen sections by seventeen wires extending substantially perpendicular to said longitudinal axis of said plates.

7. A detector apparatus for use in a scalable tomograph machine, said detector apparatus comprising a plurality of detector modules and a collimator, each of said detector modules comprising a photodiode array coupled to a scintillator array, a switching array coupled to said photodiode array, and a decoder electrically coupled to said switching array, said photodiode array having a plurality of elements arranged in rows and columns, said decoder controlling said switching array to combine outputs of said photodiode array, said scintillator array adjacent said collimator, said collimator comprising a plurality of plates, each of said plates having a longitudinal axis extending substantially parallel to a longitudinal axis of an adjacent one of said plates, and said collimator further comprising at least one wire extending substantially perpendicular to said longitudinal axis of each said plate, said wire dividing said collimator into a plurality of sections.

8. A detector apparatus in accordance with claim 7 wherein said switching array comprises a plurality of field effect transistors, wherein each field effect transistor has an input, an output, and a control line.

9. A detector apparatus in accordance with claim 8 wherein the total number of photodiode array element rows or pixels per channel is equal to n×m where n equals number of slices or field effect transistor outputs and m equals maximum number of rows per slice.

10. A detector apparatus in accordance with claim 9 wherein for a 4 slice mode of operation comprising a maximum of 4 rows of photodiode array per slice, said photodiode array comprises 16 rows or pixels per channel.

11. A detector array for a computed tomograph machine, said detector array comprising a detector housing, a plurality of detector modules, and a collimator secured to said housing, said collimator comprising a plurality of plates, each of said plates having a longitudinal axis extending substantially parallel to a longitudinal axis of an adjacent one of said plates, and having at least one wire extending substantially perpendicular to said longitudinal axis dividing the said collimator into a plurality of sections, said collimator adapted for use in a multiple slice mode of operation.

12. A detector array in accordance with claim 11 wherein for a two slice mode of operation, said collimator is divided into two sections by three wires extending substantially perpendicular to said longitudinal axis of said plates.

13. A detector array in accordance with claim 12 wherein an active area of one of said sections is approximately equal to an active area of said other section.

14. A detector array in accordance with claim 11 wherein for a multislice mode of operation, said collimator is divided into n sections by n+1 wires extending substantially perpendicular to said longitudinal axis of said plates.

15. A detector array in accordance with claim 14 wherein an active area of each of said sections is approximately equal to an active area of said other sections.

16. A detector array in accordance with claim 11 wherein each of said detector modules further comprises a scintillator array adjacent said collimator, and a photodiode array optically coupled to said scintillator array.

17. A detector array in accordance with claim 16 wherein each said scintillator array and said photodiode array is a 16×16 array.

18. A detector array in accordance with claim 16 wherein each of said detector modules further comprises a switching array coupled to said photodiode array.

19. A collimator in accordance with claim 1 wherein for a four slice mode of operation, said collimator is divided into four sections by five wires extending substantially perpendicular to said longitudinal axis of said plates.

20. A collimator in accordance with claim 19 wherein an active area of each of said sections is approximately equal to an active area of said other sections.

* * * * *